United States Patent
Dal Molin et al.

(10) Patent No.: US 8,195,281 B2
(45) Date of Patent: Jun. 5, 2012

(54) DISCRIMINATING BETWEEN TACHYCARDIAS OF VENTRICULAR ORIGIN AND SUPRA-VENTRICULAR ORIGIN, METHODS AND APPARATUS

(75) Inventors: Renzo Dal Molin, Chatillon (FR); Christine Henry, Paris (FR); Jinan El Arab, Paris (FR); Paola Bouchet, Paris (FR); Rémi Dubois, Paris (FR); Gérard Dreyfus, Gif-sur-Yvette (FR)

(73) Assignee: Sorin CRM S.A.S., Clamart (FR)

( * ) Notice: Subject to any disclaimer, the term of this patent is extended or adjusted under 35 U.S.C. 154(b) by 532 days.

(21) Appl. No.: 12/412,808

(22) Filed: Mar. 27, 2009

(65) Prior Publication Data

US 2010/0249626 A1 Sep. 30, 2010

(30) Foreign Application Priority Data

Mar. 28, 2008 (FR) ..................... 08 01691

(51) Int. Cl.
*A61B 5/04* (2006.01)
*A61N 1/00* (2006.01)
(52) U.S. Cl. ............... 600/518; 600/515; 607/4; 607/26
(58) Field of Classification Search .................. 600/515, 600/518; 607/4, 26
See application file for complete search history.

(56) References Cited

U.S. PATENT DOCUMENTS

| | | | |
|---|---|---|---|
| 5,462,060 A * | 10/1995 | Jacobson et al. | ............... 600/515 |
| 5,868,793 A | 2/1999 | Nitzsche et al. | |
| 5,891,170 A | 4/1999 | Nitzsche et al. | |
| 6,889,080 B2 | 5/2005 | Henry et al. | |
| 7,149,569 B1 | 12/2006 | Fain | |
| 7,751,873 B2 * | 7/2010 | de Voir | ......................... 600/509 |
| 2005/0159781 A1 | 7/2005 | Hsu | |
| 2006/0253162 A1 | 11/2006 | Zhang et al. | |
| 2008/0114257 A1 | 5/2008 | Molin et al. | |

FOREIGN PATENT DOCUMENTS

| | | |
|---|---|---|
| EP | 0626182 | 11/1994 |
| EP | 0813888 | 12/1997 |
| EP | 0838235 | 4/1998 |
| EP | 1208873 | 5/2002 |
| EP | 1902750 | 3/2008 |
| WO | WO 00/69517 | 11/2000 |
| WO | WO 2006/039693 | 4/2006 |
| WO | WO2006039693 | * 4/2006 |

OTHER PUBLICATIONS

Foreign Search Report (Annexe Au Rapport De Recherche Preliminaire Relatif A La Demande De Brevet Francais No. FR0801691FA705884), Apr. 15, 2010.

* cited by examiner

*Primary Examiner* — Nicole F Lavert
(74) *Attorney, Agent, or Firm* — Orrick Herrington & Sutcliffe, LLP

(57) ABSTRACT

An active medical device able to discriminate between tachycardias of ventricular origin and of supra-ventricular origin. Two distinct temporal components (UnipV, BipV) are obtained corresponding to two EGM signals of ventricular electrograms. The diagnosis operates in at least two-dimensional space to determine, from the variations of one temporal component as a function of the other temporal component, a 2D characteristic representative of a heart beat and, this, for a reference beat collected in Sinus Rhythm (SR) in the absence of tachycardia episodes, and for a heart beat in Tachycardia. The discrimination of the tachycardia type, VT or SVT, is then realized by a classifier operating a comparison of the two current and reference 2D characteristics.

29 Claims, 11 Drawing Sheets

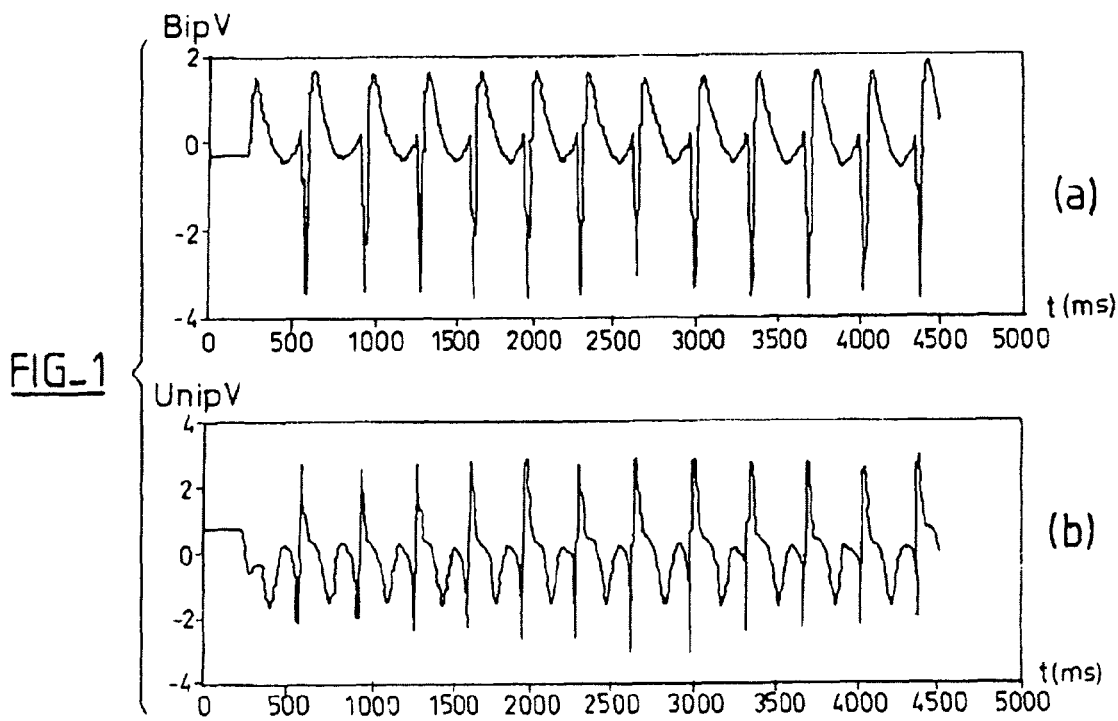
FIG_1
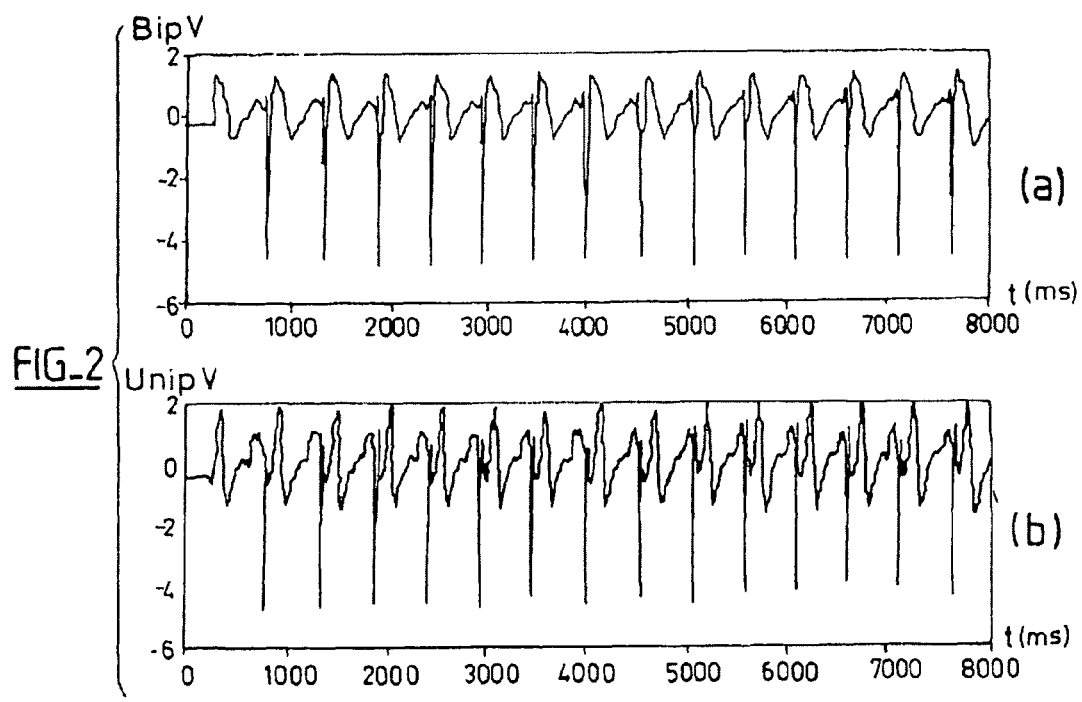
FIG_2

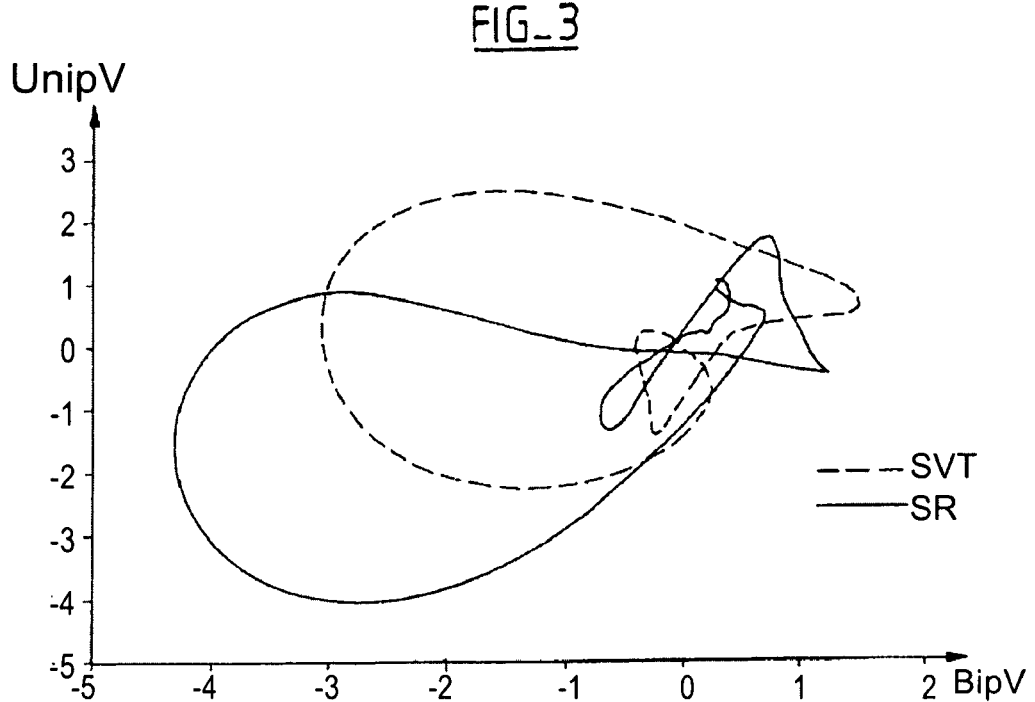
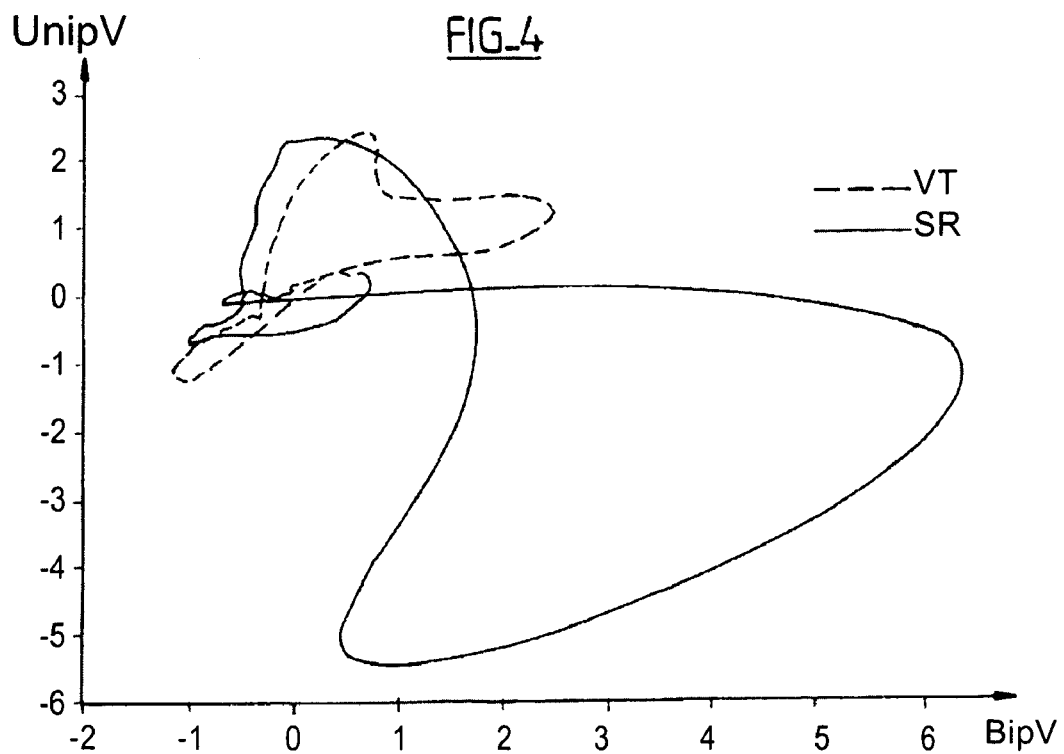

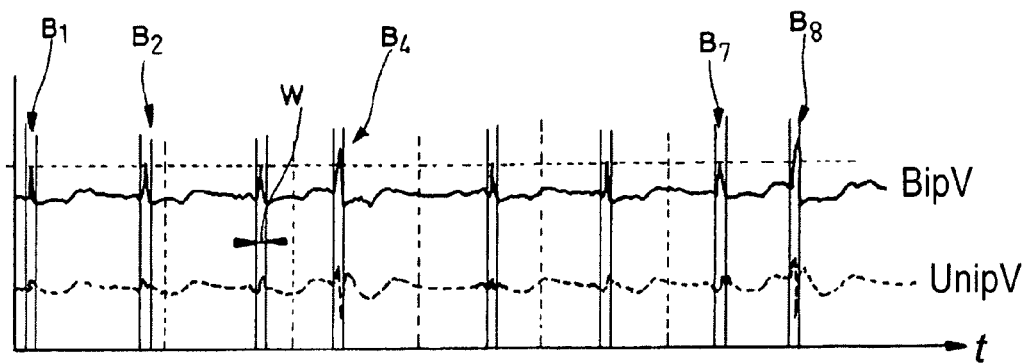
FIG_5
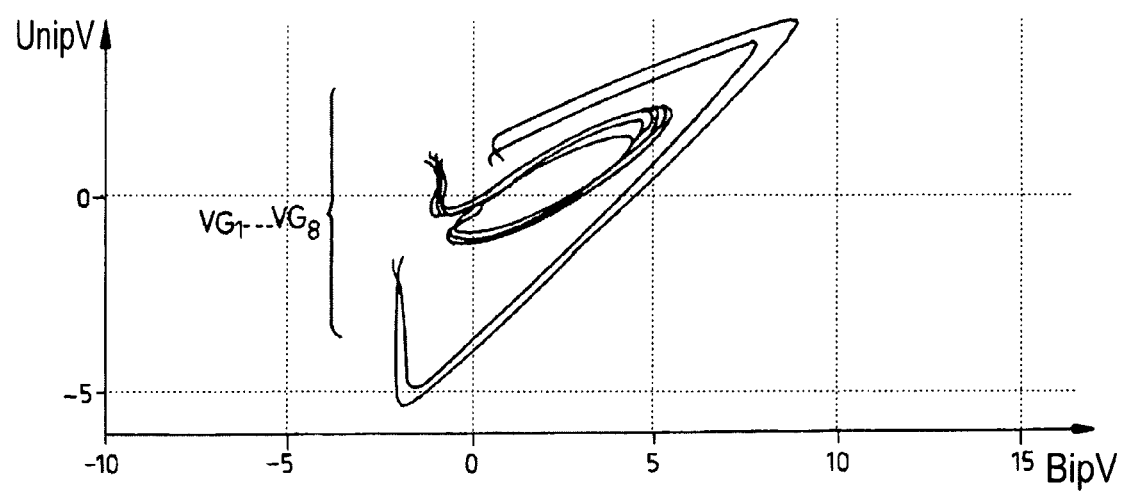
FIG_6

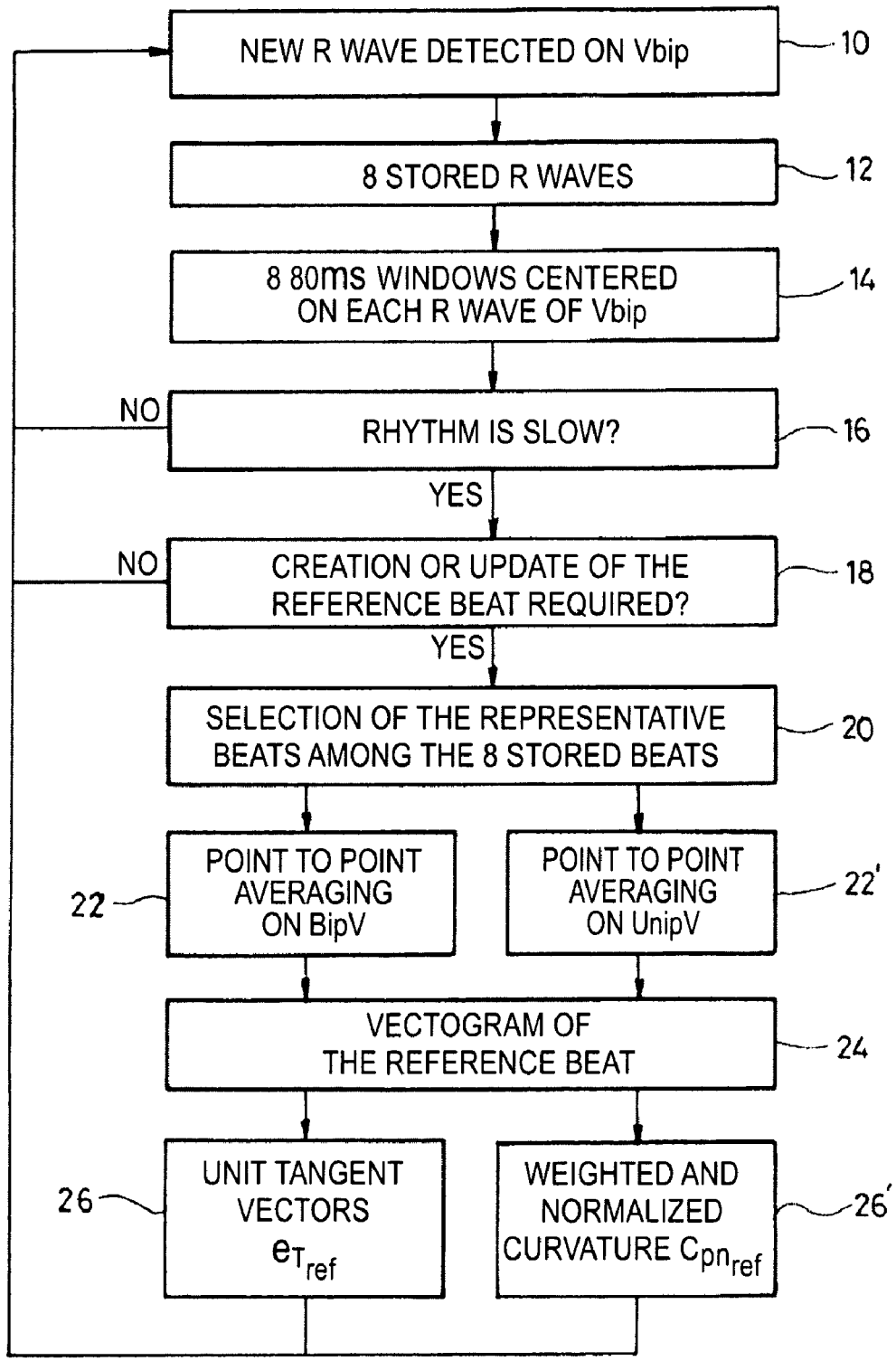
FIG_7

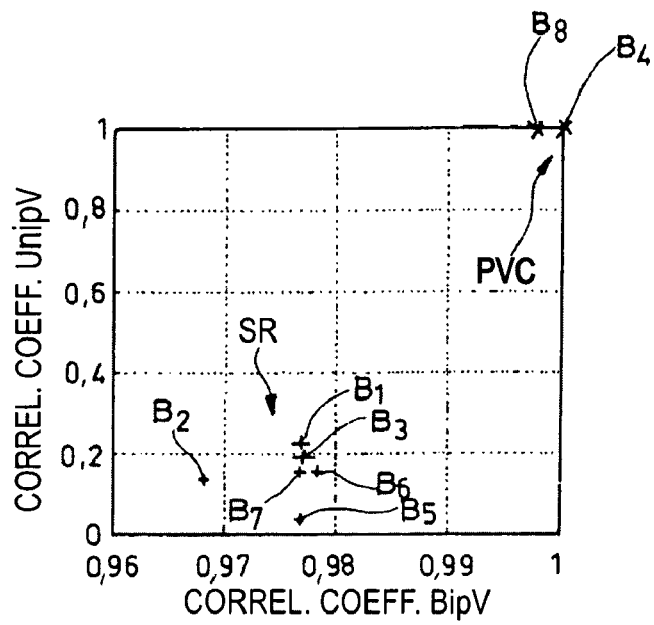
FIG_8
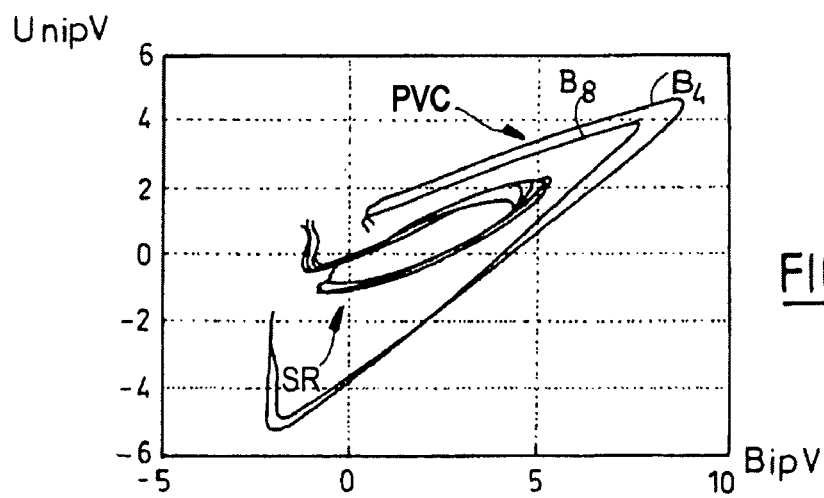
FIG_9
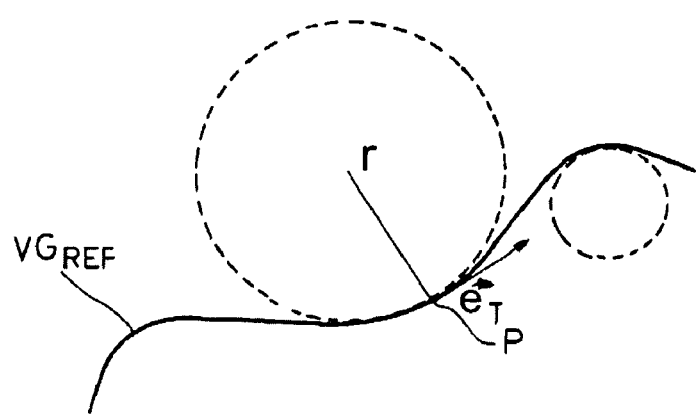
FIG_10

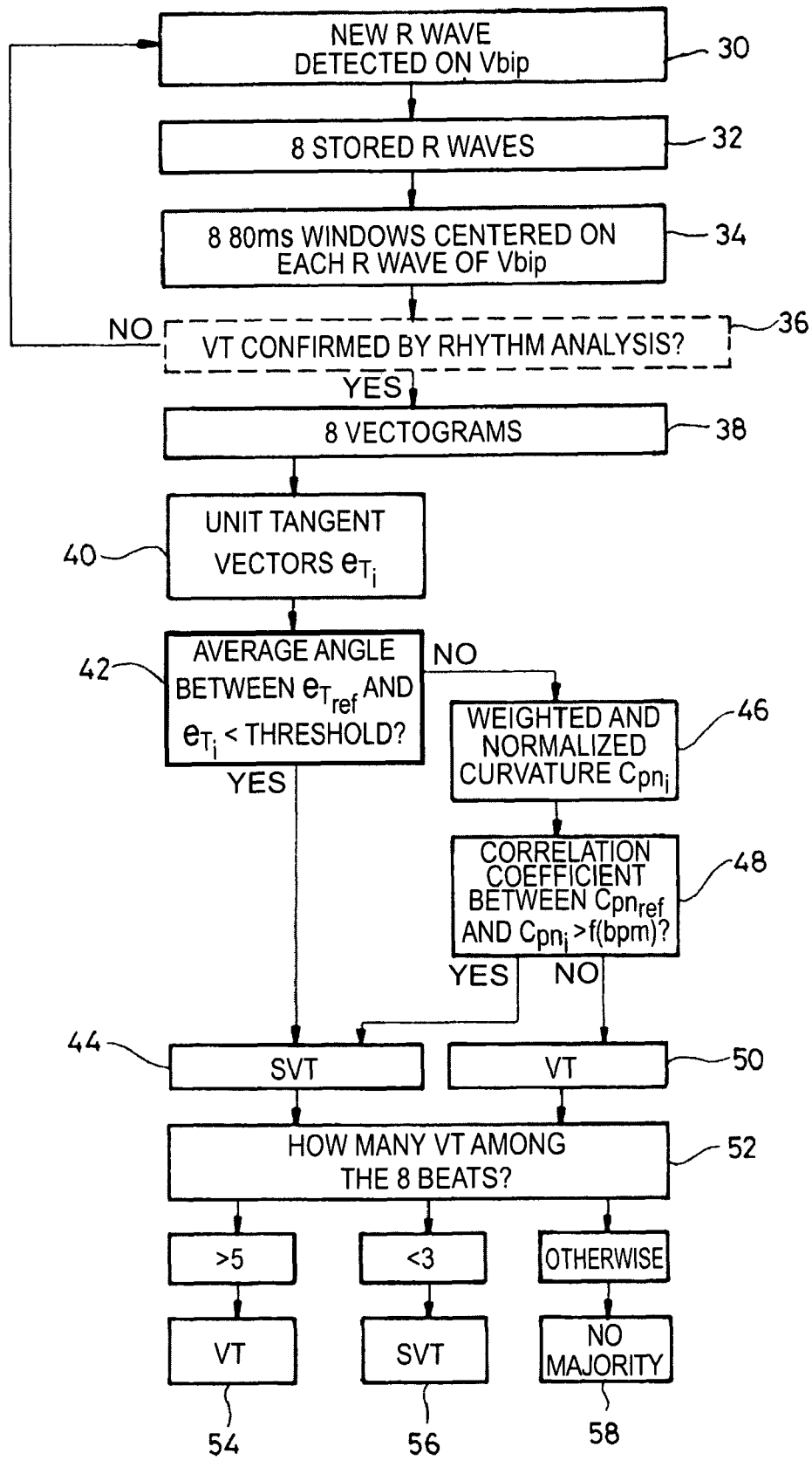

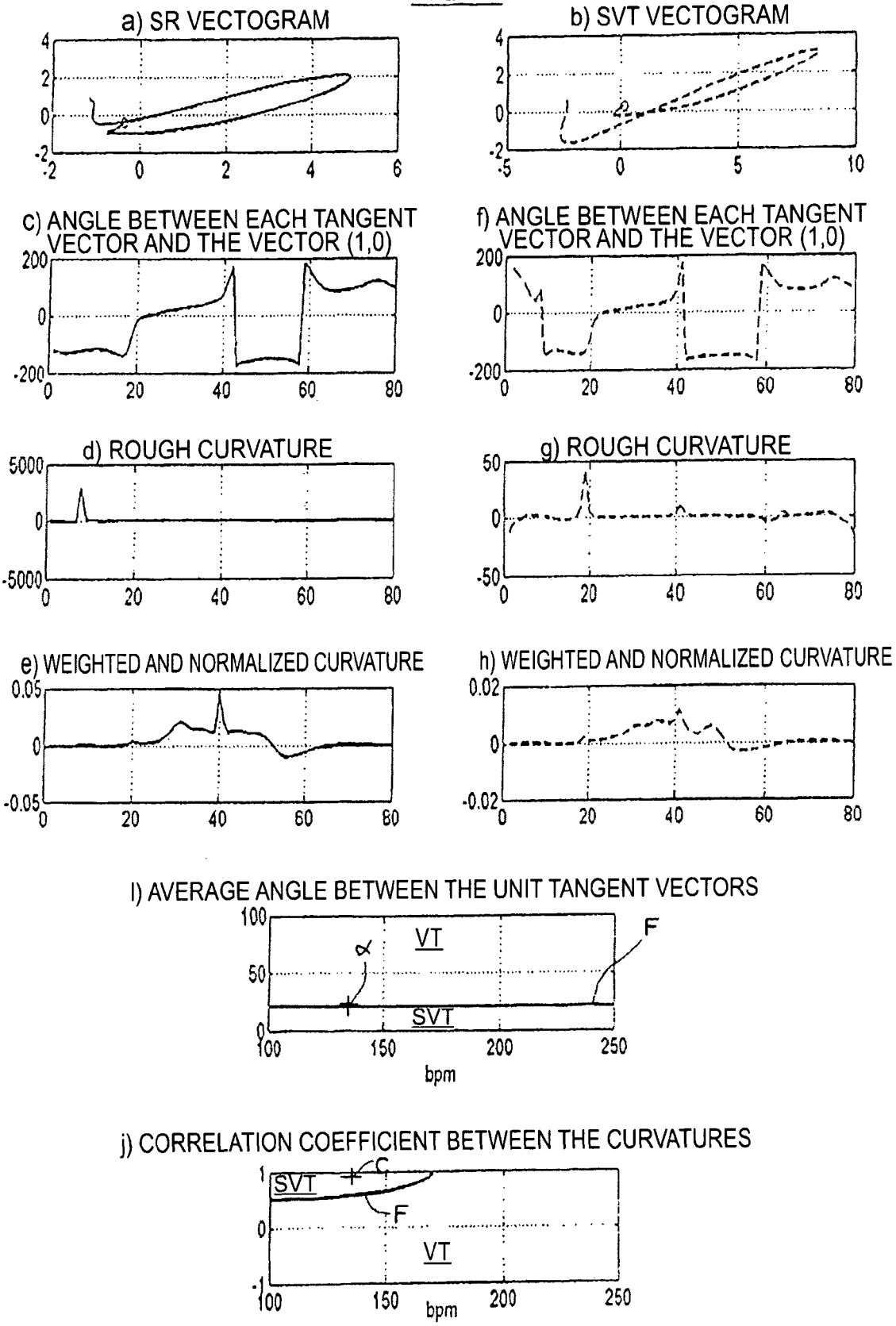

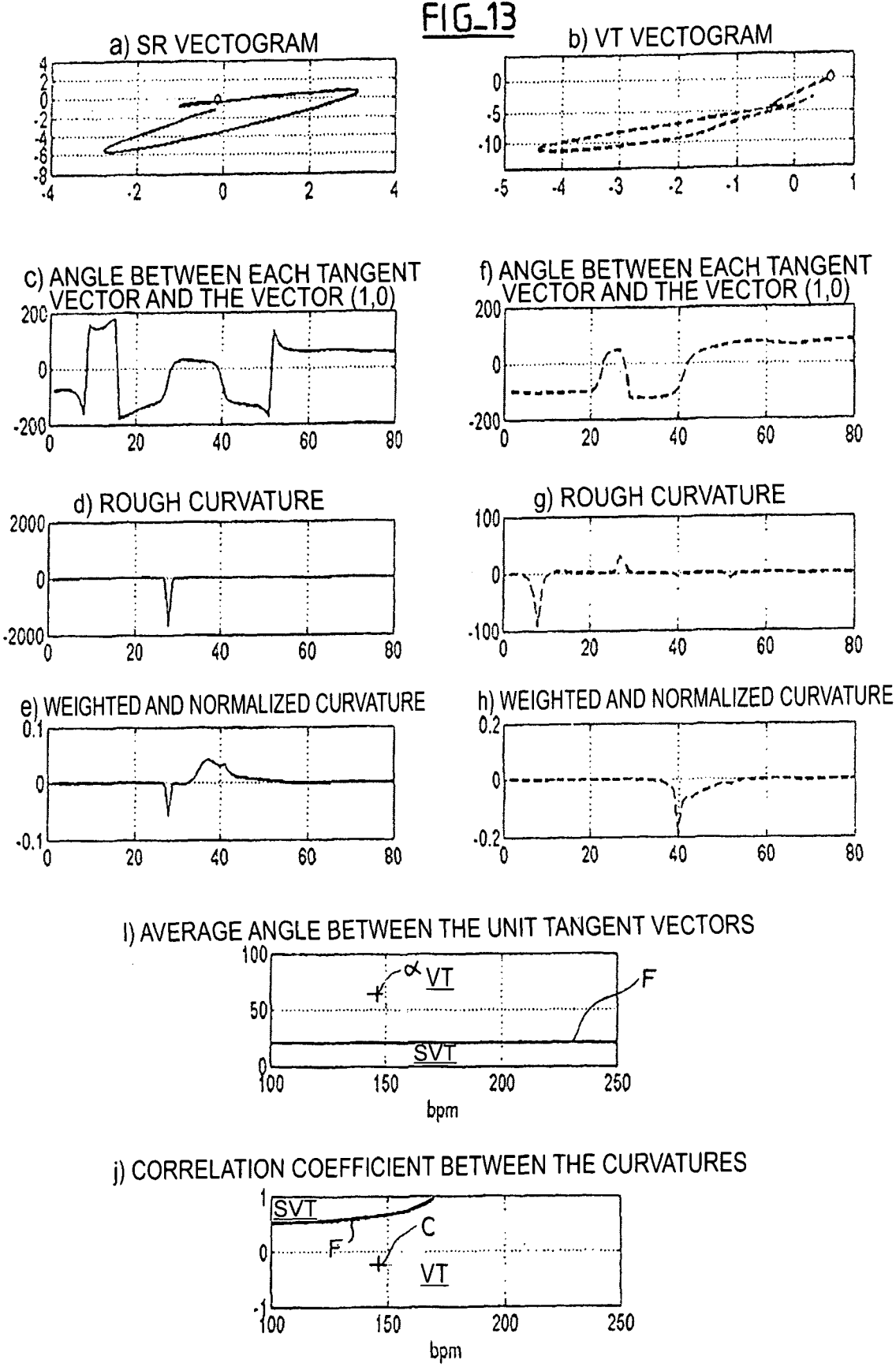

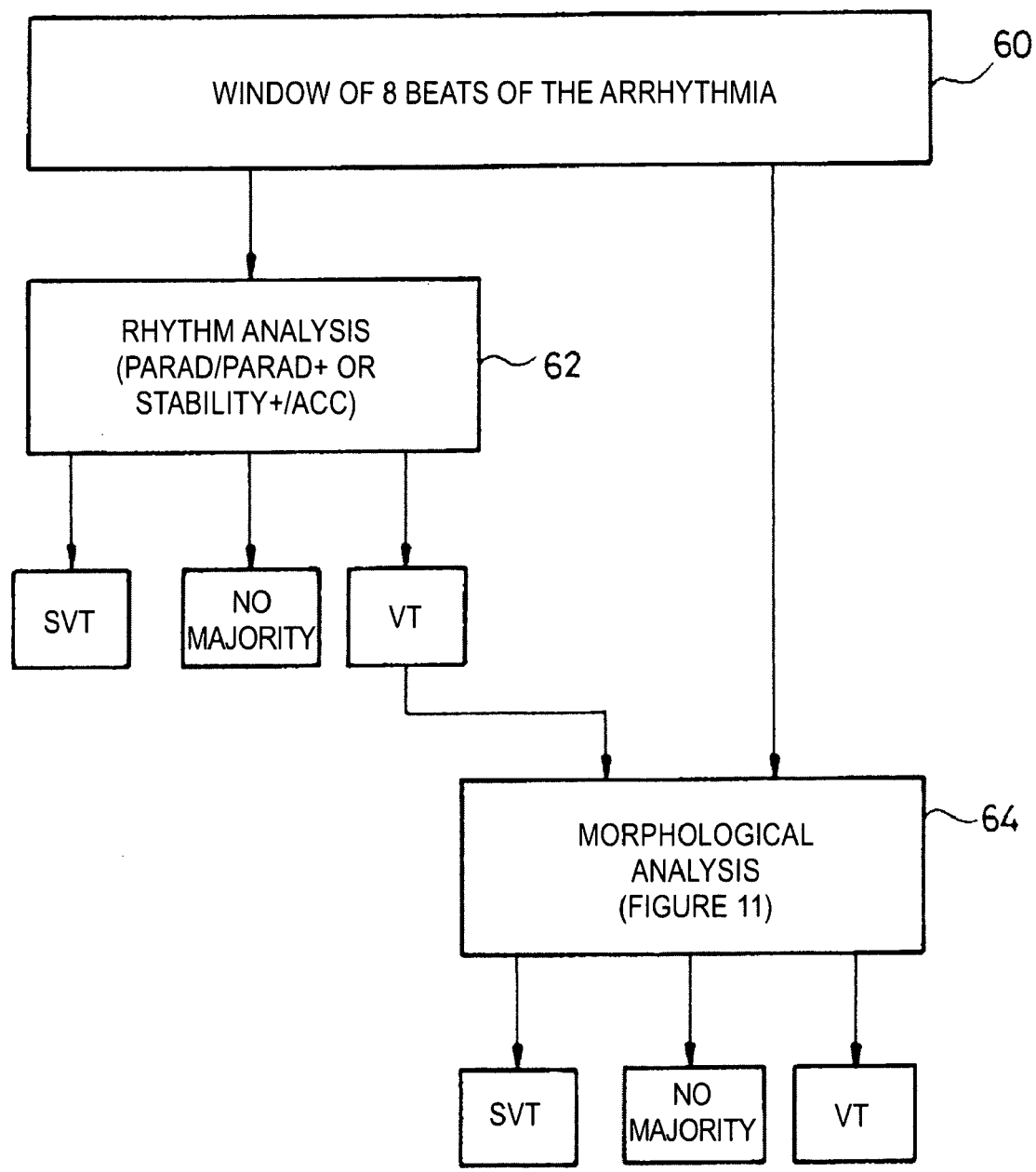

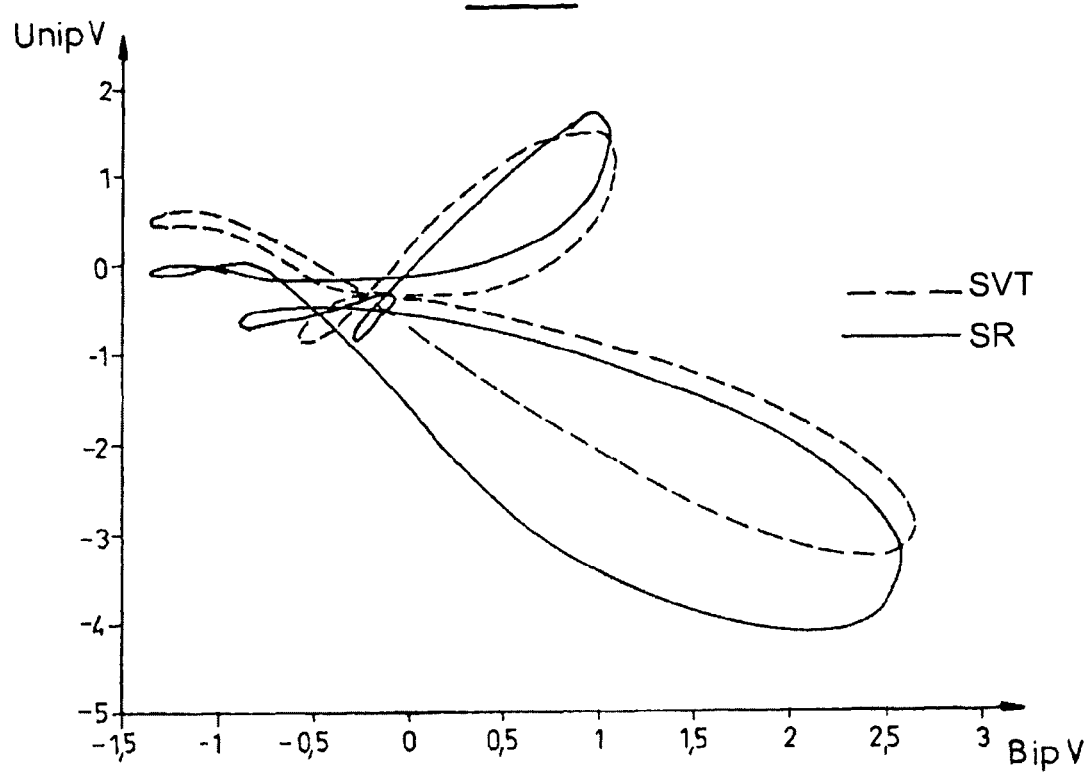
FIG_15
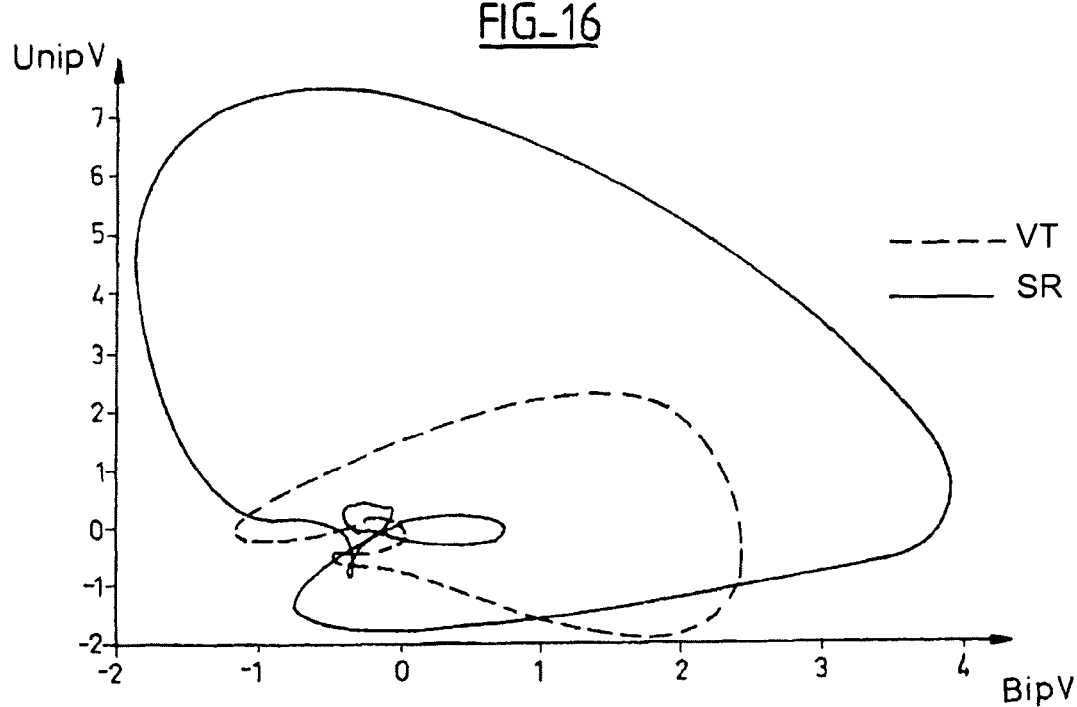
FIG_16

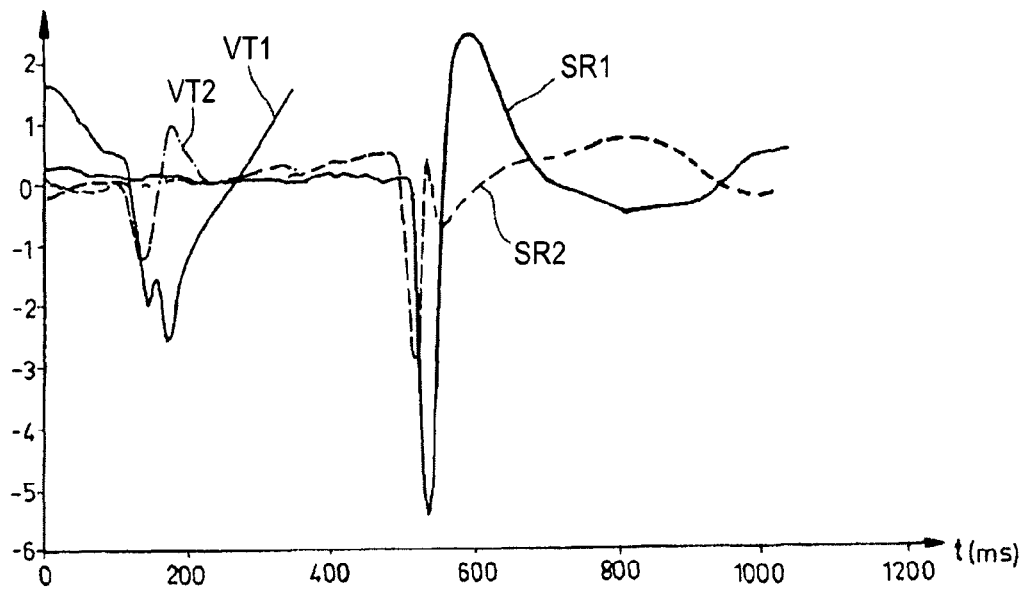
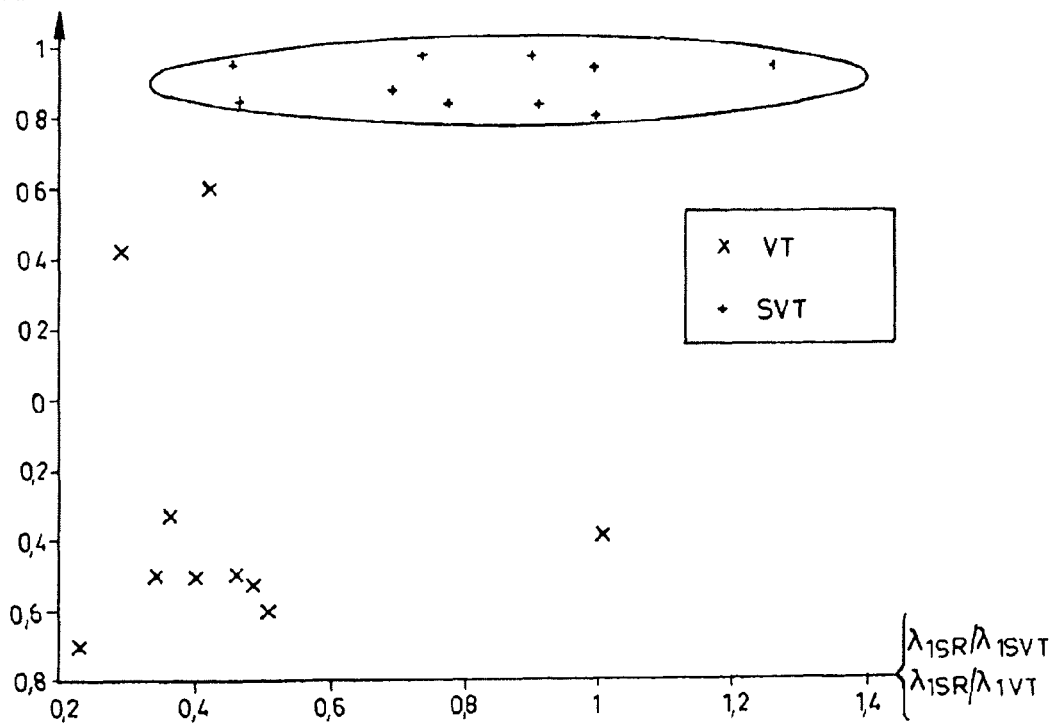

DISCRIMINATING BETWEEN TACHYCARDIAS OF VENTRICULAR ORIGIN AND SUPRA-VENTRICULAR ORIGIN, METHODS AND APPARATUS

FIELD OF THE INVENTION

The present invention relates to analyzing ventricular tachyarrhythmias, more preferably to active implantable medical devices (according to the directive 90/385/CEE dated Jun. 20, 1990) performing such analyses, and more particularly to such implantable devices that are able to apply to the heart therapies requiring the delivery of controlled, high energy electrical stimulation pulses that are designed to terminate a tachyarrhythmia and/or deliver high frequency pacing therapies known as ATP (AntiTachycardia Pacing). It should be understood, however, that the invention can be implemented not only in an implant, but also externally to the patient, for example, in an external programmer used by a physician to download and analyze the cardiac signals collected and memorized by the implant. The invention can also be implemented in a so-called "home monitoring" monitor, which is a particular type of programmer the functioning of which is entirely automated; a physician is not required with such a home monitoring monitor and this equipment can notably remotely transmit at regular or defined intervals to a distant site data collected by an implant for analysis and physician follow-up of the patient. In addition or in the alternative, the present invention can also be implemented at the data server level to operate on the rough patient data transmitted by the patient's home monitor.

BACKGROUND OF THE INVENTION

A tachyarrhythmia (also called a tachycardia) is generally an abnormal rapid cardiac rhythm that can be from a sinus, atrial or ventricular origin. More specifically, a tachycardia can encompass several varieties of cardiac rhythm disorders: when a tachyarrhythmia is present, its origin can be a ventricular fibrillation (VF), a sinus tachycardia (ST) or a Supra-Ventricular Tachycardia (SVT). The SVT includes the atrial tachycardia, the atrial flutter and the atrial fibrillation (AF). Those disorders can exist simultaneously and in that case, the patient suffers from "bi-tachycardia", notably in the presence of an atrial fibrillation combined with a Ventricular Tachycardia.

But it is not always that simple to determine the origin of an existing tachycardia. In the case of a device able to deliver a therapy such as a defibrillation shock, such a shock should only be delivered in case of a real Ventricular Tachycardia (VT) and not in the case of a Supra-Ventricular Tachycardia (SVT). Indeed, in case of SVT, the tachycardia is originated from the atrium and any shock that would be delivered would have no beneficial or therapeutic effect, because the defibrillation electrode is not implanted in the atrial area.

Further, the application of a defibrillation shock in a conscious patient is extremely nerve-racking and painful, indeed the energies applied are far above the pain threshold. In addition, delivering a defibrillation shock has adverse effects on the cardiac rhythm (risks of secondary troubles), on the functional integrity of the myocardium and, in a general way, on the physiological equilibrium of the patient. Therefore, it is desirable and important to deliver only appropriate shocks and only a defibrillation shock if a less painful therapy, such as an appropriate pacing of the atrium, can not be successfully applied.

One problem with tachycardias comes from the recognition that, in a number of pathologic cases, certain events are present, but not visible, because they are masked by other simultaneous events. For example, the wide rapid VT complex makes it difficult to recognize P waves, which does not always allow to differentiate them from a flutter associated to a functional bundle branch block. There is, therefore, a need to be able to recognize these masked phenomena and, in particular, the P waves, in this field.

But, if it is difficult for the physician, it is more difficult for automated cardiac rhythm analysis systems to make this discrimination. The discrimination criteria used in these automated devices include, in particular, the stability of the ventricular intervals (RR intervals), the analysis of the atrioventricular association (characterized by the stability of the PR interval) and the starting mode of the tachycardias (presence of a sudden acceleration and the cavity of origin, ventricular or atrial).

It is known from EP 0 626 182 A1, and its counterpart U.S. Pat. No. 5,462,060 (assigned to ELA Medical), to employ a tachyarrhythmia detection and classification algorithm named PARAD/PARAD+, implemented in particular in the Defender and Ovatio brand ELA Medical devices. Further, EP 0 838 235 A1 and its corresponding U.S. Pat. No. 5,868,793, and EP 0 813 888 A1 and its corresponding U.S. Pat. No. 5,891,170, and EP 1 208 873 A1 and its corresponding U.S. Pat. No. 6,889,080 (all three assigned to ELA Medical) describe various improvements of this algorithm, allowing to improve again the discrimination between Ventricular Tachycardia and Supra-Ventricular Tachycardia, notably to avoid a false positive diagnosis (indication of a Ventricular Tachycardia when the disorder is a Supra-Ventricular Tachycardia) or a false negative diagnosis (indication of a Supra-Ventricular Tachycardia when the disorder is a Ventricular Tachycardia).

Other proposals have also been made to discriminate between Ventricular Tachycardia and Supra-Ventricular Tachycardia, based on a morphologic analysis of the QRS complex alone, hence without using the P wave that is difficult to recognize. Those techniques based on a morphological analysis of the QRS are the more often used by cardiologists in clinical practice, when they analyze an ECG diagram to characterize the ventricular arrhythmias, which are generally the more threatening ones.

But the application of such methods to automated detection algorithms embedded in implanted cardiac prosthesis is not considered reliable enough, in part because the potential information contained in the endocardial electrogram signals (EGM), collected by these devices, is not completely controlled and is less controlled than the ECG signals collected by an external recorder. In particular, the normality parameters of these signals are widely unknown, which does not allow discriminating by comparison between the pathological situations and the others.

In addition, the analysis algorithms are complex and, often, require incompatible requirements, in terms of calculation (computing) power and energy consumption, for a miniaturized implanted device. This leads to propose sub-optimal solutions based on algorithms, which do not allow a sufficiently reliable diagnosis.

Various algorithms for implantable defibrillators, based on a morphological analysis, are known to exist. These algorithms implement methods based on the following property: during a Supra-Ventricular Tachycardia episode, the electrical pulses are conducted in the ventricles by the same conduction paths as in Sinus Rhythm, so that the morphology of the ventricular contraction signal is very similar to that of the signal recorded in Sinus Rhythm. On the other hand, during a Ventricular Tachycardia episode, the conduction paths are different, and the recorded electrical signal is different. Hence, those known methods propose to discriminate VT/SVT by the measurement of the similarity of the recorded signals during the arrhythmia with the recorded signals in Sinus Rhythm.

US 2005/0159781 A1 (Cardiac Pacemakers, Inc.) describes a technique named "VTC" (electrogram Vector Timing and Correlation), in which the algorithm analyses the amplitude and the temporal position of a certain number of singular points, representative of a QRS complex collected on an endocardial EGM channel, typically on the right ventricle (RV). Before this, the algorithm creates a Sinus Rhythm reference beat, by: (i) collecting a certain number of complexes from a unipolar RV signal (between the can (e.g., the case of the implant) and an electrode on the lead), (ii) aligning these complexes by the use of a corresponding bipolar RV signal (collected between two electrodes on the lead), (iii) calculating an average value of the complexes aligned in this manner and, finally, (iv) extracting from the average reference beat eight representative points (minimum, maximum, inflection point . . . ) to define a model or "template". After that, when an arrhythmia is detected, the VTC algorithm calculates the correlation coefficient between these eight reference points from the model and the eight analog points from each tachycardia beat collected on the (one) unipolar RV signal channel. If, for a given tachycardia, the algorithm identifies a sufficiently high number of non correlated beats, then the tachycardia is classified as being of a ventricular origin—which can then justify the application of a defibrillation shock. In the case of a dual chamber defibrillator, the VTC morphological analysis algorithm can be improved, by taking into account additional non morphological criteria (V>A and stability).

Another method, named "MD" (Morphology Discrimination) and described in U.S. Pat. No. 7,149,569 B1 (Pacesetter Inc.), uses an algorithm which intends to calculate a matching percentage below a model beat and each beat of the arrhythmia to be analyzed, this percentage being a function of the amplitude, of the polarity and of the order of the peaks. If at least five beats among eight have a matching percentage below a threshold value, then the arrhythmia is characterized as being a tachycardia originated from the ventricle (the threshold can be programmed with values comprised between 30% and 95%). The clinical studies nevertheless show that this algorithm must be programmed so that it also takes into account non morphological criteria (acceleration, stability), so as to provide satisfactory results.

WO 00/69517 A1 (Medtronic Inc.) describes a third method, named Wavelet Dynamic Discrimination, which concerns comparing the morphology of a basic rhythm and the morphology of the tachycardia, based on the difference between wavelet coefficients, this difference being a matching percentage. The beats for which this percentage is below 70% are classified as originated from the ventricle, after which a tachycardia is classified as being originated from the ventricle if at least six beats out of eight fulfill this criteria.

All in all, whatever the implemented technique, until now, the proposed algorithms all are exposed to being deluded in certain particular clinical situations, and resulting in, as a consequence, a wrong Ventricular Tachycardia diagnosis and, so, the risk of delivering an inappropriate therapy.

OBJECTS AND SUMMARY OF THE INVENTION

It is, therefore, an object of the present invention to overcome the above-referenced drawbacks, by proposing an improved analysis technique that minimizes the risk of false VT diagnosis (false positive or false negative) during the discrimination between VT and SVT, hence to reduce the number of inappropriate shocks due to a wrong discrimination, and consequently ensuring a greater reliability in the tachyarrhythmia analysis.

In other words, the object of the present invention is to improve the decision-making of an implantable defibrillator in the discrimination between VT and SVT, by improving the specificity while maintaining the sensitivity.

Broadly, the present invention is based on the assessment that all the relevant parameters to discriminate between a VT and a SVT can be obtained by analyzing EGM signals originated from the same cavity (e.g., the ventricle) collected simultaneously on two distinctive channels, those signals being combined in the form of two respective components applied to a bi-directional analysis—which means without taking directly into account time dimension. The two different EGM channels are, for example, one from a unipolar signal (collected between the can and one of the distal and the proximal electrodes), and one from a bipolar signal (collected between the distal and proximal electrodes).

It should be understood that the present invention is not limited to a "bi-dimensional" analysis or an analysis "in two dimensions" (2D as discussed in detail herein), but rather that these are illustrative embodiments and indeed the invention applies also in a multi-dimensional space (3D or more), by extrapolation of the teachings of the present description to a situation where the EGM signals from a same cavity are collected simultaneously on three or more channels.

The invention proposes, as with the prior known methods, to perform the VT/SVT discrimination based on a measure of the matching of recorded signals during the arrhythmia with those recorded in Sinus Rhythm. Advantageously, in a characteristic manner of the present invention this VT/SVT discrimination is performed using a "cardiac loop" or "vectogram", which is the representation of one of those signals as a function of the other, in a two-dimensional space. This space is typically a "unipolar channel (in ordinate) versus bipolar channel (in abscissa)". Each current heart beat (or optionally each significant fraction of a heart beat) is then represented by its vectogram in the plane so defined. In case of arrhythmia, the current heart beat is compared to a reference vectogram, collected in Sinus Rhythm. The algorithm estimates the similarity between the current and the reference vectograms and, consequently, discriminates the arrhythmia type, VT (low similarity) or SVT (high similarity).

Broadly, the present invention proposes an improvement to an active medical device of the type described in US 2005/0159781 A1. One aspect of the present invention is directed to an active medical device, having circuits and control logic signal processing for collecting an electrical activity of a patient's heart and producing at least two distinct temporal components corresponding to two EGM signals of a ventricular electrogram and that is able to detect a presence of a tachycardia episode in the collected electrical activity, diagnose a ventricular tachyarrhythmia, and discriminate in the detected tachyarrhythmia between a Ventricular Tachycardia originated in the ventricle and a Supra-Ventricular Tachycardia, wherein the improvement comprises:

producing a first and a second distinct temporal component from two distinct EGM signals of a ventricular electrogram;

conducting a bi-dimensional analysis, able to determine, from the variations of one of said first and second temporal components as a function of the other of said first and second temporal components, a 2D characteristic representative of a heart beat; and discriminating between a Ventricular Tachycardia and a Supra-Ventricular Tachycardia by comparing:

a first current 2D characteristic, representative of a tachycardia beat (SVT, VT), from said two EGM signals collected during a tachycardia episode, with a second reference 2D characteristic, representative of a Sinus Rhythm (SR) heart beat from said two EGM signals.

Preferably, the bi-dimensional analysis is conducted using a temporal window (W) including the QRS complex of the cardiac beat and determining the 2D characteristic based on said temporal components occurring during said window W.

In one embodiment, the diagnosis determines the reference 2D characteristic from a plurality of averaged successive heart beats. More preferably, in the diagnosis "non-representative" beats in that plurality of cardiac beats are detected and excluded from the determination of the reference 2D characteristic. The detection of the non-representative beats can be obtained by performing a morphological analysis of the plurality of cardiac beats by a cross-correlation, for example, by identifying by clustering of the representative beats.

In yet another embodiment, the discrimination of tachycardias is performed by charactering the current and reference 2D characteristics by at least one geometrical descriptor ($\vec{e}_T$, c), and comparing the current and reference 2D characteristics by the determined geometrical descriptor. The geometrical descriptor is, for example, the unit tangent vector ($\vec{e}_T$) to the 2D characteristic, also called normalized velocity vector, considered at a plurality of points. More preferably, this discrimination involves evaluating an average angle between unit tangent vectors to respectively the current 2D characteristic and the reference 2D characteristic. Alternatively, the geometrical descriptor can be the norm of the velocity vector of the 2D characteristic, considered in a plurality of points. More preferably, this discrimination involves evaluating a correlation coefficient between the norms of the velocity vectors of respectively the current 2D characteristic and the reference 2D characteristic. Finally, the geometrical descriptor can be the curvature (c) of the 2D characteristic, considered in a plurality of points, and more preferably, the discrimination involves evaluating a correlation coefficient between the respective curvatures of the current 2D characteristic and the reference 2D characteristic.

An alternate preferred embodiment employs a bi-dimensional analysis in which is determined a reference mark orthonormal to an axis corresponding to a main axis of the patient's heart. The reference mark is preferably determined by analyzing a sinus EGM signal collected in the absence of tachycardia episodes. Also, a reference change, from a primitive reference to that reference mark, can be applied to the first and second 2D characteristics.

In this embodiment, the diagnosis can include analyzing the main axis components and producing first descriptor parameters of the morphology of said first and second 2D characteristics. The first descriptor parameters may be selected from among the group consisting of: first and second eigen values of a covariance matrix associated to each of these eigen values; orientation of the main and secondary axis; a ratio between the extreme signal amplitudes on each of the channels; and an area circumscribed by the 2D characteristic.

In an alternate embodiment, the diagnosis can include producing a first and a second one-dimensional component by projection of each of the first and second 2D characteristics on the axis of the reference mark. The diagnosis in this case can produce second descriptor parameters of the morphology of said first and second one-dimensional components. The second descriptor parameters are selected from among the group consisting of: a signal maximum height; a signal minimum height; and a signal width.

In a still further variation, the diagnosis can be performed by means for providing an inter-correlation between said first and second 2D characteristics. The inter-correlation provides a bi-dimensional distribution analysis between the correlation coefficients and the eigen values of the covariance matrix of an analysis in main components.

Alternatively, the inter-correlation may be employed to provide a three-dimensional distribution analysis, able to define, for at least one descriptor parameter of the morphology of the first and second 2D characteristics, a discriminator plane between ventricular originated tachycardias and supraventricular originated tachycardias. The inter-correlation, can use a linear classifier or an adaptive neural network classifier for performing said three-dimensional distribution analysis.

In yet another embodiment, the diagnosis is performed so as to be essentially devoid of any analysis in main components. This can be achieved, for example, by determining ratios between a maximum amplitude and a minimum amplitude of a depolarization complex for each of said two distinct temporal components, respectively for said Sinus Rhythm and tachycardia beats, or by determining some correlation maximum between said 2D characteristics from said Sinus Rhythm and tachycardia heart beats.

BRIEF DESCRIPTION OF DRAWINGS

Further features, advantages and characteristics of the present invention will now be described in connection with the following detailed description of preferred embodiments of the present invention, made with reference to the attached drawings in which the same numerical references designate identical or functionally similar elements, and in which:

FIG. 1 illustrates representative electrogram signals collected on the ventricular bipolar and ventricular unipolar channels, respectively, for a patient in Sinus Rhythm;

FIG. 2 illustrates representative electrogram signals collected on the ventricular bipolar and ventricular unipolar channels, respectively, for a patient in a Supra Ventricular Tachycardia episode;

FIG. 3 illustrates the cardiac loops collected by combining the two signals of the FIGS. 1 and 2 for a same patient, in Sinus Rhythm and during a Supra-Ventricular Tachycardia episode;

FIG. 4 illustrates the cardiac loops collected by combining two signals, for a same patient in Sinus Rhythm and during a Ventricular Tachycardia episode, analogously to FIG. 3;

FIG. 5 illustrates a first embodiment of the invention in which electrogram signals typically collected on the ventricular bipolar and ventricular unipolar channels are simultaneously recorded for a given patient;

FIG. 6 illustrates a vectogram collected by combining the two signals of FIG. 5, for eight successive beats;

FIG. 7 is a flow-chart illustrating a process for a reference beat estimation algorithm in Sinus Rhythm;

FIGS. 8 and 9 illustrate how the correlation between the beats is analyzed, designated to discriminate between a heart beat in Sinus Rhythm and premature ventricular contractions;

FIG. 10 illustrates two parameters of characterization of a vectogram in a given point, namely the radius of curvature and the tangent vector at that point;

FIG. 11 is a flow-chart illustrating a process for the morphological classification algorithm designed to determine the nature, ventricular or supra-ventricular, of a detected tachycardia in a patient;

FIGS. 12*a*-12*j* graphically illustrate the different parameters calculated by the characterization algorithm for a same patient, respectively in Sinus Rhythm and during a Supra-Ventricular Tachycardia episode, as well as a method to analyze these parameters in order to deduce the nature of this tachycardia;

FIGS. 13*a*-13*j* are homolog to what is illustrated in FIGS. 12*a*-12*j* for a patient in Sinus Rhythm but during a Ventricular Tachycardia episode;

FIG. 14 is a synopsis flow chart showing the method by which the morphological analysis according to a preferred embodiment of the present invention can be combined to a rhythm analysis to improve the specificity of an existing device;

FIG. 15 illustrates, for a second embodiment of the present invention, collected cardiac loops, in the case of a Sinus Rhythm and in the case of a Supra-Ventricular Tachycardia respectively, when the components of these loops are projected in the base defined by the Sinus Rhythm;

FIG. 16 is homolog to FIG. 15 for a Sinus Rhythm, but for a Ventricular Tachycardia;

FIG. 17 illustrates the variations of the signals corresponding to a Sinus Rhythm and to a Ventricular Tachycardia, when these signals are projected on the main axis and on the secondary axis of a cardiac loop, said axis being determined by an analysis in principal components, according to the second mode of implementation of the invention; and FIG. 18 illustrates a technique allowing, after a correlation analysis, to discriminate between Ventricular Tachycardia and Supra-Ventricular Tachycardia made from the correlation results, according to a second embodiment of the present invention.

DETAILED DESCRIPTION OF THE INVENTION

With reference to the drawings, two preferred embodiments of the present invention will be hereinafter described, applied to an active implantable medical device, allowing to continuously monitor the cardiac rhythm and deliver to the heart, as necessary, in case of rhythm trouble detected by said implant, electrical stimulation pulses for resynchronization and/or defibrillation.

As regards the software aspects, the present invention can be implemented by an appropriate programming of the control software of a known device, for example, a device of the cardiac stimulation, resynchronization, or defibrillator type, such device having suitable circuitry to acquire a signal provided by the endocardial leads.

The invention can preferably be applied to implantable devices such as the devices of the Ovatio brand commercialised by ELA Medical, Montrouge, France. These are devices having a programmable microprocessor to which it is possible to transmit by telemetry software applications which will be downloaded and embedded in associated memory and executed to implement the functions of the invention as described herein. The adaptation of these known implantable devices to the implementation of the functions of the present invention is believed to be within the abilities of a person of ordinary skill in the art and, therefore, will not be described in detail.

As described above, a preferred embodiment of the present invention provides an analysis technique for operating a discrimination between Ventricular Tachycardia (VT) and Supra-Ventricular Tachycardia (SVT) from the EGM electrogram signals collected on two distinctive channels and analyzed in two dimensions.

With reference to FIG. 1, in the case of a patient with a Sinus Rhythm (SR) the BipV and UnipV electrogram are illustrated, observed respectively on the ventricular bipolar (FIG. 1*a*) and on the ventricular unipolar (FIG. 1*b*) channels. With reference to FIG. 2, in the same manner, the BipV and UnipV corresponding signals are illustrated in the case of a patient in SVT. Those signals are subjected to an appropriate filtering, normalizing and centering pre-processing (this pre-processing signal conditioning, classical in itself, forms no part of the present invention and therefore is not described in detail).

Once these signals are collected (in the time domain), the next step is tracing one of the signals as a function of the other. The created characteristic, named a "cardiac loop", is illustrated in FIG. 3, on one hand in the case of a Sinus Rhythm (loop in continuous line) and on the other hand in the case of a SVT (loop in dotted line), in the same patient. Each of these loops is representative of a complete heart beat, either in Sinus Rhythm, or in SVT. It should be understood, however, as described below, that it is not mandatory to analyze the complete heart beat, and that the analysis of a significant portion of this heart beat (typically, a portion centered on or about the QRS complex) is generally sufficient to operate the expected discrimination.

By comparing the two cardiac loops illustrated in FIG. 3, it can be pointed out that the Sinus Rhythm loop (corresponding to a beat in Sinus Rhythm) and the SVT loop (corresponding to a beat in Supra-Ventricular Tachycardia) have some similarities in terms of loop direction, loop orientation, propagation direction, as well as their shape and the circumscribed area.

On the other hand, with reference to FIG. 4, the collected loops illustrated in the case of a patient in Sinus Rhythm (continuous line loop) with episodes of VT (dotted line loop), the VT loop is significantly different than the one collected in SR, and it can be pointed out there is little or no similarity.

The invention mainly proposes to systematize this approach by analyzing the 2D vectogram characteristics by comparison to a corresponding reference vectogram, collected in a Sinus Rhythm.

First Embodiment of the Present Invention

An analysis method and apparatus in accordance with a first embodiment of the present invention, will now be described with reference to FIGS. 5 to 14. In this embodiment, after each detection of a bipolar signal depolarization peak BipV (corresponding to a detected R wave), the corresponding beat is isolated by a permanent window $W_{QRS}$ having a duration of several tens of milliseconds centered on the determined depolarization peak, for example, a width window $W_{QRS}$=80 ms corresponding to 80 points for a sampling frequency of 1000 Hz. This typical 80 ms value allows to appropriately isolate the QRS complex to analyze its morphology, without inducing too much noise around, said noise corresponding to the base line after the end of the QRS.

The device keeps stored in memory a plurality of successive beats, for example, the last eight beats B1 to B8, as illustrated in FIG. 5, those beats being recorded simultaneously on the ventricular bipolar channel (BipV) and on the ventricular unipolar channel (UnipV). The portion of each of these beats comprised inside the window $W_{QRS}$ is then represented by a vectogram, considered in the plane formed by the bipolar channel in abscissa and by the unipolar channel in ordinate. It shall be pointed out that the vectogram corresponding to each of these beats is not a closed loop, because it corresponds only to a portion of the complete cardiac loop, that portion being the QRS complex isolated inside the $W_{QRS}$ window.

The analysis requires the creation of a reference beat, preferably averaged from a succession of beats in Sinus Rhythm, to be used in the discrimination.

However, it is necessary, even in the absence of a tachycardia, to exclude certain non-significant beats: on the drawn vectograms illustrated in FIG. 6, it can be noticed that two among the eight vectograms $VG_1 \ldots VG_8$ have a significantly different form than the other six: they correspond to premature ventricular conductions or PVC (specifically beats B4 and B8 on FIG. 5). Such beats must be identified and excluded from the calculation of the average reference beat, because their morphology is in no way representative.

Referring to FIG. 7, a Sinus Rhythm analysis and determination of a representative reference beat algorithm is illustrated. For each detection of an R wave on the bipolar channel (step 10), the device stores the eight successive waves (step 12) and isolates the QRS complex in the window $W_{QRS}$ for each of the collected beat on the bipolar channel (step 14).

In the absence of a tachycardia (tested at step 16), the algorithm determines whether it is required or not to create or update the reference beat (step 18). Indeed, even if there is still a reference heart beat, it can be desirable to recalculate it on a regular basis (typically at least once a day, or at least every hour after the implant so as to take into account the electrode maturation phenomenon after the lead implant), and/or according to the status of the patient (rest/exercise . . . ).

When it is required to create or recalculate the reference heart beat, the algorithm selects the representative beats among the eight memorized beats, by isolating and removing the PVC and the various artifacts such as improperly centered windows. A first simple method to select the representative beats concerns keeping only the complexes for which the RR intervals are stable, and to average point by point the complexes fulfilling these criteria. Another method, illustrated with reference to FIGS. 8 and 9, concerns analyzing the morphology of the eight beats by cross-correlation. To that purpose, a beat is randomly selected as the reference, for example, the fourth of the eight beats illustrated in FIG. 5 (which is a PVC). A correlation coefficient is calculated between this reference beat and each of the seven other beats, for both the bipolar signal and the unipolar signal. The corresponding correlation coefficients $C_{BipV}(i,4)$ and $C_{UnipV}(i,4)$ of each beat Bi can then be represented in a plane by a point which abscissa is $C_{BipV}(i,4)$ and which ordinate is $C_{UnipV}(i,4)$, the point corresponding to the fourth beat (i=4) being the point (1,1).

If all the correlation coefficients are higher than 0.9, then the reference beat in slow rhythm is calculated by averaging point by point the eight beats, this being performed for each of the bipolar and unipolar channels (step 22 and 22' on FIG. 7). On the other hand, if there are values below 0.9 (as in the case of the illustrating example), then an iterative algorithm of unsupervised clustering is applied to these eight points, for example, a K-means algorithm. Such an algorithm, in itself well-known, portions the data in K homogeneous classes, minimizing the intra-class variance so as to obtain, in an iterative method, some clusters based on the Euclidian distance between the points. Referring to FIG. 8, it can be noticed that the points can be brought together in two clusters, in the upper right and lower left regions of the plot. For each point, if its distance to the center of the cluster is greater than half of the distance between the two respective clusters, than it will be considered that this point does not belong to any cluster. (Note that this is not the case in the example illustrated on FIG. 9, where the intra-cluster distance is notably below half of the inter-cluster distance). Finally, the algorithm selects the cluster which contains the most elements, which is the lower left cluster on FIG. 8.

The reference beat in slow rhythm is calculated on each of the two bipolar and unipolar channels (steps 22 and 22') by averaging point by point the beats corresponding to the selected clusters: in the example, the vectograms referenced as "Sinus Rhythm" in FIG. 9, corresponding to the "Sinus Rhythm" clusters of FIG. 8, will be averaged point by point to get the reference beat, whereas the two vectograms referenced as "PVC" on FIG. 9, corresponding to the beats B4 and B8 of the "PVC" cluster of FIG. 8, will be eliminated, because they correspond to PVC (or to artifacts).

From these point by point average values of the beats on the bipolar and unipolar channels, the algorithm then determines a vectogram of the reference beat (step 24, of FIG. 7), by representing in abscissa the variations of the bipolar channel and in ordinate the variations of the unipolar channel, for each of the sampling points of the signals inside the window W. This vectogram is then characterized in each of its points.

The invention proposes, for example, to realize this characterization by two descriptors: the unit tangent vector $\vec{e}_T$ and the curvature c (which is the inverse of the radius of curvature r) at the point P of the reference vectogram $VG_{REF}$, and this for the successive different sampled points of the vectogram (steps 26 and 26', of FIG. 7). Another possible descriptor is the norm of the velocity vector.

The unit tangent vector $\vec{e}_T$ at a given point can be determined by a known technique, preferably with a discrete filter which approximates the first derivatives, for example, on four points for a sampling frequency of 1000 Hz. This filtering is then typically followed by a normalization (so that the tangent vector is unitary).

The curvature c can be calculated in a given point of the vectogram from the first derivatives and from the second derivatives, preferably calculated with the same method as for first derivatives. Favourably, to give more importance to the interesting zones of the vectogram where the points are the more distant, the curvature is then weighted by a power of the distance between the points. This distance is calculated from a discrete filter applied to the Euclidian distances in the vectogram space between two successive points. Finally, the curvature is normalized.

The reference vectogram has then been determined and characterized by its tangent vector and its curvature in each point.

In the case of a tachycardia, the device will then be able to determine the nature of this tachycardia by a morphological analysis involving a comparison with the reference vectogram as defined.

The general tachycardia classification algorithm is illustrated on FIG. 11. The device detects and memorizes the eight last beats, more preferably by keeping the only information centered on a window $W_{QRS}$ around the bipolar signal depolarization peak (steps 30, 32 and 34). The method to be used is the same as the one described above with reference to FIG. 5, the steps 30, 32 and 34 being similar to the steps 10, 12 and 14 previously described.

The algorithm can eventually decide to continue the morphological analysis on the basis of the existence of a VT previously confirmed by the rhythm analysis (test 36); for example, by the known algorithms such as PARAD, PARAD+ or STABILITY+ as implemented in the above-described ELA Medical devices and described in the above-cited documents EP 0 626 182 A1 and corresponding U.S. Pat. No. 5,462,060 (ELA Medical) and others. The combination of the rhythm analysis and of the morphological analysis will be described hereafter with reference to FIG. 14, nevertheless, it can be pointed out that a prior detection of a VT by the rhythm analysis, before the morphological analysis is performed, is not a necessary characteristic to implement the invention and, consequently, the step 36 is an optional step.

The next step (step 38) concerns drawing the vectograms of the last eight beats and to characterize them in each of their points by the two descriptors (unit tangent vector and weighted and normalized curvature).

The comparison between a vectogram collected in tachycardia with the reference vectogram collected in Sinus Rhythm for the same patient is performed by the calculation of two quantities:

the average angle α between the unit tangent vectors of both respective vectograms and the correlation coefficient cc between the curvature of the two respective vectograms.

The discrimination between VT and SVT will be operated on the values of α and of cc, for example, by comparison with the previously determined decision thresholds from a learning base. Thus:

if the average angle α is below a given value (steps 40 and 42), or if the correlation coefficient cc is higher than a given threshold depending of the heart rate (steps 46 and 48), then the beat corresponding to the arrhythmia is classified as being from a supra-ventricular origin (step 44);

otherwise, it is classified as being from a ventricular origin (step 50).

The correlation coefficient threshold corresponds to a heart rate quadratic function, this function being calculated on the complete training set by classical methods of supervised classification, such as the least square method. The supervised classification concerns establishing from a sample of classified data a decision frontier separating the two classes by minimizing the square error (as defined in the least square method) between the true values (for example, +1 for VT and −1 for SVT) and the values predicted by the classifier.

The next step (step 52) compares the results collected for each of the eight successive beats:

if at least six of the eight beats are classified as being from a ventricular origin, the arrhythmia, at this stage, is classified as being from a ventricular origin, according to the morphological analysis (step 54);

if at least six of the last eight beats are classified as being from a supra-ventricular origin, the arrhythmia, at this stage, is classified as being from a supra-ventricular origin, according to the morphological analysis (step 56);

otherwise, the arrhythmia is not classified, insofar as the morphological analysis does not reveal any majority or significant trend (step 58).

FIGS. 12 and 13 display two examples of classification in accordance with the present invention, respectively for a first patient in Sinus Rhythm and during a SVT episode, and for a second patient in Sinus Rhythm and during a VT episode:

FIGS. 12a and 13a respectively display the vectograms corresponding to two reference beats, calculated as above in Sinus Rhythm for the two respective patients;

FIG. 12b illustrates the vectogram in SVT from the first patient, and FIG. 13b illustrates the vectogram in VT of the second patient.

FIGS. 12c, 12d and 12e respectively display, for the vectogram of the reference beat of the first patient (vectogram from FIG. 12a): the variations of the average angle between the unit tangent vector and the abscissa axis; the rough curvature; and the weighted and normalized curvature;

FIGS. 13c, 13d and 13e are homolog to FIGS. 12c, 12d and 12e, for the vectogram of the reference beat of the second patient (vectogram from FIG. 13a);

FIGS. 12f, 12g and 12h are homolog to FIGS. 12c, 12d and 12e, for the vectogram of the first patient collected during a supra-ventricular arrhythmia episode (vectogram from FIG. 12b);

FIGS. 13f, 13g and 13h are homolog to FIGS. 12f, 12g and 12h, for the vectogram of the second patient collected during a supra-ventricular arrhythmia episode (vectogram from FIG. 13b);

FIGS. 12i and 13i respectively indicate the average angle α between the unit tangent vectors during an arrhythmia and in Sinus Rhythm, compared with the decision frontier F between VT and SVT; and FIGS. 12j and 13j indicate the correlation coefficient cc between the vectogram curves during arrhythmia and during Sinus Rhythm, compared with the decision frontier F between VT and SVT.

In the case of the first patient (FIG. 12), the analysis of the unitary tangent vectors is not sufficient to conclude whether it is a SVT (on FIG. 12i, the point α is too near from the frontier F), but the analysis of the curvature confirms it is a SVT indeed (FIG. 12j). For the second patient, the two criteria clearly show it is a VT (FIG. 12i and FIG. 13j).

With reference to FIG. 14, a synopsis is shown illustrating how it is possible to combine rhythm analysis (according to known techniques) and morphological analysis (according to the invention) to allow the device to make a global decision on the arrhythmia classification, and therefore on the opportunity to apply or not a defibrillation shock to the patient.

For the application of a dual chamber defibrillator, the morphological analysis is notably useful when the atrioventricular association is in 1:1, because in that case the acceleration is sudden and the origin of this acceleration is not obvious (atrial tachycardia (SVT)/Ventricular Tachycardia). Or again when the RR intervals are stable and that there is no atrioventricular association (atrial fibrillation (SVT)/Ventricular Tachycardia), because the rhythm analysis is often not sufficient to determine for sure the origin of the arrhythmia.

For the application of a single chamber defibrillator, the morphological analysis allows to avoid some inappropriate shocks. Indeed, the conjunction of a situation with stable RR intervals, sudden acceleration and absence of long cycle, considered by the rhythm analysis as requiring a therapy, can characterize in certain situations a Supra-Ventricular Tachycardia, which does not justify such a therapy. The morphological analysis according to the present invention will allow discriminating such a situation.

With reference to FIG. 14, from eight successive beats collected during an arrhythmia (step 60), the device operates simultaneously a rhythm analysis (step 62) and a morphological analysis (step 64 according to the method described above with respect to FIG. 11). The rhythm analysis operates the classification between VT, SVT or non significant arrhythmia (no majority on the eight beats) and the morphological analysis does the same.

Favourably, the morphological analysis is executed or taken into account only if the rhythm analysis concludes that the arrhythmia is originated from the ventricle (VT). In that case, the aim of the morphological analysis is to avoid an inappropriate shock, with the hypothesis that the sensitivity of the rhythm analysis is really equal to one:

if the rhythm analysis concludes that the tachyarrhythmia is from supra-ventricular origin (SVT) or undetermined (absence of majority), then no therapy will be triggered, regardless of the result of the morphological analysis;

if, on the contrary, the rhythm analysis concludes that the tachyarrhythmia is from a ventricular origin (VT) and that it is persistent, then the therapy will be triggered only if the morphological analysis confirms the ventricular origin of this arrhythmia, when the later is detected as well as during the persistence (e.g., twelve cycles in the VT zone).

Second Embodiment of the Present Invention

With reference to FIGS. 15 to 18, another embodiment of the present invention is now described. This second embodiment is also based on the analysis and the characterization of the vectogram, but based on other criteria than those described above with respect to the first embodiment (unit tangent vector and weighted and normalized curvature in each point). The considerations related to the possible method for combining rhythm analysis and morphological analysis, described in particular in relation with FIG. 14, are nevertheless applicable to this second embodiment.

In this second embodiment, the orthonormal basis in which the vectogram UnipV=f (BipV) with be represented is defined by an analysis in principal components (an analysis named "ACP") from the Sinus Rhythm. This ACP analysis, which is well-known in itself, can be performed for each beat, and it allows for deducing the electrical heart axis, which is an indicator of the general direction of propagation of the electrical wave in the ventricles. The path with the highest dynamic is the one in which the propagation is the greatest, with the corresponding direction being named the "main axis". The main axis can be complemented by two other "secondary" axes that are perpendicular with each other and with the main axis.

In the present embodiment, the analysis will be performed in two dimensions only (which means only one secondary axis will be considered). Indeed, as described hereafter, the present invention technique allows discriminating between VT and SVT from two electrodes only, which advantageously allows the implementation of this technique in a single chamber defibrillator.

However, despite the fact the analysis of a 2D characteristic is sufficient to reach the expected result, in an alternate implementation the analysis can be performed on the basis of a 3D characteristic, collected from three electrodes.

The principal components in the ACP analysis that allows defining the reference orthonormal basis will now be described. Let S1 and S2 be the two signals of the A (BipV) and B (UnipV) respective channels representing an averaged heart beat, for example, on fifteen successive sinus beats. Each signal is constituted by N points represented in the basis of the electrodes (A, B), ($S_1$ (i), S2 (i)) being the coordinates of the $I^{th}$ point.

For the analysis in principal components, it is considered the N points are approximated by an ellipse, which allows calculating:

the axis of this ellipse constituting the ACP basis,
the length of each of them.

Those two values allow, on one hand to identify the main direction of the ellipse (and consequently the spreading direction of the vectogram) and on the other hand to quantify its dimensions and its area.

Next, a study is made to determine the coordinates of these N points in the ACP basis ($P_1$, $P_2$), which requires calculating a transition matrix from the basis (A, B) to the basis ($P_1$, $P_2$).

The transition matrix is calculated by diagonalizing the covariance matrix C associated to the N points. Calculating the covariance matrix is equivalent to approximating the N points as a part of an ellipse. By diagonalizing this matrix, one gets:

the axis of this ellipsis, defined by the eigen vectors of C, and the length of each of these axis, indicated by the corresponding eigen value.

The eigen vector having the greatest eigen value thus defines the direction of the greatest dispersion of collection of points.

Then, the eigen values $(\lambda_i)_{i=1,2}$ and the eigen vectors (V1, V2) associated to the C matrix are calculated. One calculates the D matrix defined by:

$$D = P^{0.1} \cdot C \cdot P$$

In which D is the diagonal matrix of the eigen values:

$$D = \begin{bmatrix} \lambda_1 & 0 \\ 0 & \lambda_2 \end{bmatrix}$$

And in which P is the transition matrix from the basis ($P_1$, $P_2$) to the basis (A, B) constituted of the eigen vectors of C. Thus, the inverse matrix of P is defined by:

$$P^- = [P_1 P_2]$$

in which $P_i$ is the column vector i in the ACP basis (that is to say the eigen vector associated to the $\lambda_i$ eigen value) expressed in the basis (A, B). By classifying the $\lambda_i$ in the decreasing order, the $P_1$ vector represents the direction, in which the collection of points is the most dispersed, and the $P_2$ vector the second direction. The $(S_1^{ACP}, S_2^{ACP})$ signal in this new basis ($P_1$, $P_2$) is defined by:

$$[S_1^{ACP}, S_2^{ACP}] = P^{-1} \cdot \begin{bmatrix} S_1 \\ S_2 \end{bmatrix}$$

As indicated above, according to the present invention, the ACP basis is calculated on the basis of the Sinus Rhythm, before projecting the Sinus Rhythm data and the tachycardia data in this same basis.

FIG. 15 illustrates the result resulting of a basis change, for a patient in Sinus Rhythm (loop in continuous line) with SVT episodes (loop in dotted line). FIG. 16 is homolog to FIG. 15, for a patient in Sinus Rhythm (loop in continuous line) with VT episodes (loop in dotted line). By comparing FIGS. 15 and 16, it can be observed a very narrow similarity between the Sinus Rhythm loops and the TSV loops on the direction, orientation, shape, area and morphology, while no significant similarity can be observed between the Sinus Rhythm loops and the VT loops.

The next step of the analysis determines a certain number of descriptive parameters of the morphology of these loops, so as to be able to operate, in the best conditions, a discrimination between VT and SVT for a patient having tachycardia episodes. The analysis in principal components performed at the previous step can notably be used to extract the following descriptive parameters (the method to determine these parameters will be described hereafter):

the main axis, which is the eigen vector of the covariance matrix associated to the greatest eigen value;

the secondary axis, which is the eigen vector of the covariance matrix associated to the second eigen value;

the dimensions of these two axis, which are the two eigen values of the covariance matrix;

the angles between the two axis with the OX axis, extracted from the calculations of the sines and cosines.

In order to extract from the ACP analysis descriptive mathematic parameters of the loop morphology, each signal (Sinus Rhythm and tachycardia) is then projected on its own basis, so as to be able to observe the corresponding one dimension signal (which is therefore a signal in the time domain), then compare the shapes in order to extract the morphological parameters which differentiate the SVT from the VT.

FIG. 17 illustrates those signals in one dimension:

the referenced lines $SR_1$ and $VT_1$ represent the ACP components projected on the main axis of the reference mark, respectively for a Sinus Rhythm beat and for a Ventricular Tachycardia beat;

the referenced lines $SR_2$ and $VT_2$ correspond to the same respective ACP components on the secondary reference mark.

Once this step is performed, it is possible to extract representative parameters, such as:

maximum height of the signals (on the two axes, main and secondary);

minimum height of the signals (on the two axes, main and secondary);

width of the signals (on the two axes, main and secondary). From these morphological parameters, the algorithm then calculates correlation coefficients between, on one hand the Sinus Rhythm and Supra-Ventricular Tachycardia signals and, on the other hand, those coefficients being calculated on the main and the secondary channels. The average square error compared to the Sinus Rhythm is also calculated, for the Supra-Ventricular Tachycardia beats and for the VT beats. The distribution obtained in the two cases of tachycardia is illustrated, with reference to FIG. 18, where are displayed:

in abscissa, the ratio of the eigen values on the main channel of the Sinus Rhythm and of the SVT or of the VT, and in ordinate, the correlation coefficient between SR and SVT or between SR and VT.

This distribution shows that the data collected in the case of a VT and in the case of a Supra-Ventricular Tachycardia are very well separated and that it is thus possible to operate a classification of the tachycardias and a relevant discrimination by implementing, for example, a linear classifier or a neural classifier, in accordance with a process that will be described hereafter.

The descriptive parameters of the 2D loop morphologies that can be used to operate this classification of the tachycardias will now be described in more detail. From the patient's Sinus Rhythm EGM:

the first eigen value $\lambda_{1,SR}$ and the second eigen value $\lambda_{2,SR}$ of the analysis calculation in principal components;

the $\theta_{SR}$ angle between the first main axis of the beat and the first recording channel;

the $R_{1,SR}$ ratio between the depolarisation complex maximum and minimum amplitudes on the first main channel; and the $R_{2,SR}$ ratio between the depolarisation complex maximum and minimum amplitudes on the second channel.

In the same way, for tachycardia beats (VT or SVT) it is possible to obtain the following parameters:

the first eigen value $\lambda_{1,TR}$ and the second eigen value $\lambda_{2,TR}$ from the analysis calculation in principal components;

the $\theta_{TR}$ angle between the first main axis of the beat and the first recording channel;

the $R_{1,TR}$ ratio between the depolarisation complex maximum and minimum amplitudes on the first main channel; and the $R_{2,TR}$ ratio between the depolarisation complex maximum and minimum amplitudes on the second channel.

For the comparison of the sinus beat and of the tachycardia beat the following representative parameters can be used:

maximum of correlation $M_1$ on the first main channel between the line of Sinus Rhythm beat and the line of the first tachycardia beat;

maximum of correlation $M_2$ between the lines on the second main channel; and/or mean squared error MSE between the two beats on the first main channel.

From these parameters, it is possible to calculate various representative expressions designated below as D1 to D5. The D1 expression below, which is the ratio of the first and second eigen value calculation of principal components, reflects the shape of the vectogram loop associated with the beat, so the form report between sinus beats strongly and tachycardia beat:

$$\cdot D_1 = \frac{(\lambda_1/\lambda_2)_{SR}}{(\lambda_1/\lambda_2)_{TR}}$$

The term D2 below reflects the ratio between the fraction of the information contained on the main track for the sinus beat and the one contained on the main track for the tachycardia beat ($\lambda_1/(\lambda_1+\lambda_2)$) reflecting the proportion of information expressed by the main track in relation to the total information available on both channels):

$$D_2 = \frac{(\lambda_1/(\lambda_1+\lambda_2))_{SR}}{(\lambda_1/(\lambda_1+\lambda_2))_{TR}}$$

If we designate $\theta$ as the angle formed by the main axis with the first track recording, the D3 expression below reflects the directions of propagation of the beat in Sinus Rhythm and in tachycardia:

$$D_3 = \frac{\theta_{SR}}{\theta_{TR}}$$

Finally, the D4 and D5 expressions below highlight the differences of the traces on the first main track and the second main track of the two Sinus Rhythm and tachycardia beats $$D_4 = \frac{R_{1,SR}}{R_{1,TR}}, D_5 = \frac{R_{2,SR}}{R_{2,TR}}$$

The discrimination between VT and Supra-Ventricular Tachycardia can then be performed by various types of classifiers, in particular by a linear classifier or a neural classifier. A first mode of implementation builds a linear classifier in the 3D space formed by such three descriptors MSE, M1 and D1 (this method also being applicable to the use of other descriptors). Such a classifier is characterized by the equation of the plane separating in this space the two families of arrhythmias, VT and SVT.

A robust plane separator can be obtained by minimization of least square of the distance of each sample to the plane. The equation of the plane, characterized by its orthogonal vector A is:

$$\left\langle A_1 \begin{bmatrix} EQM \\ M_1 \\ D_1 \\ 1 \end{bmatrix} \right\rangle = 0 \Leftrightarrow A_1 EQM + A_2 M_1 + A_3 D_1 + A_4 = 0$$

A is calculated from the coordinates of the base by:

$$A = (X^T X)^{-1} X^T Y$$

The matrix X is the matrix containing for each of arrhythmias the value of the three descriptors in columns, and a fourth column of 1. This matrix has the following structure, assuming that there is a database of patients with from 1 to N arrhythmias:

$$\begin{matrix} MSE(1) & M_1(1) & D_1(1) & 1 \\ MSE(2) & M_1(2) & D_1(2) & 1 \\ \vdots & \vdots & \vdots & \\ MSE(N) & M_1(N) & D_1(N) & 1 \end{matrix}$$

The matrix Y is the vector consisting of −1 when the point corresponds to a Supra-Ventricular Tachycardia and of +1 if the point corresponds to a VT.

O is the matrix that contains the new value of the descriptors in columns and a fourth column of 1 to classify an arrhythmia and Z is the matrix defined by:

$$Z = A^t O.$$

If Z is negative, the arrhythmia is classified as a SVT; if z is positive the arrhythmia is classified as a VT.

Alternatively, in order to simplify calculations and reduce the workload of the processor, it is possible to apply most of the principles described in the above without using principal component analysis. Thus, reports $R_{1,SR}$ and $R_{2,SR}$, respectively between the maximum and minimum amplitude of the depolarization complex on the axes BipV and UnipV from the patient's Sinus Rhythm EGM, as well as the ratio $R_{1,TR}$ and $R_{2,TR}$ for the tachycardia beats can be determined without using principal component analysis. In the same way may the maximum of correlation M1 and M2 between the Sinus Rhythm beat route and the tachycardia beat route be determined, respectively of the BipV and UnipV axes. Based on the values so determined, then it is possible to deduce D4 and D5 values, for further analysis on the basis of these descriptors, as described in the preceding paragraphs.

The database is scalable and is continuously filled in the device, each arrhythmia being added or taking the place of an arrhythmia of the database. Also, the device, implant or programmer, recalculates on a regular basis the matrix A.

The device may include complementary means to post check the classification of the arrhythmia, for example:

If the device detects a VT by the method of linear classification, it notifies the patient by a beep. If the VT disappears, the classification was erroneous;

If the device detects a SVT which becomes a Ventricular Fibrillation, the classification was erroneous; and If the device makes a misclassification of an arrhythmia, an ECG record like a Holter, allows to detect it, the physician indicates it by telemetry to the defibrillator.

The device having proved a misclassification of an arrhythmia can either:

add the arrhythmia to the data base, replace an arrhythmia of the same type in the data base and then recalculate the matrix A.

Another mode of realization can, alternatively, implement a neural classifier, which notably allows operating by means of an adaptive network, instead of a pure mathematical calculation. This classifier is constructed in the 3D space, for example, using the three descriptors MSE, M1 and D1 (this method also being applicable to the use of other descriptors).

Such a classifier is characterized by the equation of the plane separating in that space the two arrhythmia families, VT and SVT:

$$y = f(W^T \phi)$$

$$y = +1 \text{ if } W^T \phi \geq 0;$$

$$y = -1 \text{ if } W^T \phi > 0$$

W being the vector constituted of weights applied to each descriptor;

φ being the vector including for an arrhythmia in columns the value of the three descriptors and the bias 1 (MSE, M1, D1, 1);

y being the predictor: if y is negative the arrhythmia is classified as a Supra-Ventricular Tachycardia, if y is positive the arrhythmia is classified as a VT.

The value of W is determined by the deterministic gradient algorithm by applying the following rule:

. W is initialized;

The learning is performed on a set of arrhythmias previously classified and confirmed:

if the prediction is good W is not modified if for a Supra-Ventricular Tachycardia $\phi_n$ the prediction is wrong, W is subtracted from the value $\phi_n$;

if for a Ventricular Tachycardia $\phi_n$ the prediction is wrong, W is added to $\phi_n$ The data base is scalable and is continuously filled in the device, each arrhythmia either being added or replacing an arrhythmia in the data base. Furthermore, the device, implant or programmer, redoes on a regular basis the learning of W.

Here again, the device can include complementary means to post verify the classification of the arrhythmia, of the same type as those exposed above, leading to new learning of W on a regular basis in the case of classification errors.

One skilled in the art will appreciate that the present invention may be practiced by other than the embodiments described herein, which are provided for purposes of illustration and not of limitation.

We claim:

1. An active medical device comprising:
   a. a means for collecting an electrical activity of a patient's heart, including a means for producing at least two distinct temporal components corresponding to two distinct EGM signals of a ventricular electrogram; the collecting means further comprising means for producing a first and a second distinct temporal components from said two distinct EGM signals of ventricular electrogram;
   b. a means for detecting a presence of a tachycardia episode the two distinct EGM signals of a ventricular electrogram; and
   c. a diagnosis means for diagnosing a ventricular tachyarrhythmia including means for discriminating in the detected tachycardias between a Ventricular Tachycardia and a Supra-Ventricular Tachycardia the diagnosis means further comprising:

i. a means for conducting a bi-dimensional analysis, able to determine, from a variation of one of said first and second temporal components as a function of the other of said first and second temporal components, a 2D characteristic representative of a heart beat; and ii. discriminator means further comprising means for comparing:
1. a first current 2D characteristic, representative of a tachycardia beat wherein the two EGM signals collected are during a tachycardia episode, and
2. a second reference 2D characteristic, representative of a Sinus Rhythm beat wherein the two EGM signals are collected from non-tachycardia episodes.

2. The device of claim 1, wherein the EGM signals include a QRS complex and the means for conducting the bi-dimensional analysis further comprises a temporal window ($W_{QRS}$) including a QRS complex of said heart beat and means for determining said 2D characteristic based on said temporal components occurring during said window.

3. The device of claim 1, wherein the diagnosis means further comprises means for determining said reference 2D characteristic from a plurality of averaged successive heart beats.

4. The device of claim 3, wherein the diagnosis means further comprises means for detecting not representative beats in said plurality of heart beats, and excluding said not representative beats from the determination of the reference 2D characteristic.

5. The device of claim 4, wherein the means for detecting the non-representative heart beats further comprises means for performing a morphological analysis of said plurality of heart beats by a cross-correlation.

6. The device of claim 5, wherein the means for performing a morphological analysis further comprises means for identifying by clustering of non-representative beats.

7. The device of claim 1, wherein the discriminator means further comprises means for characterizing said current and reference 2D characteristics by at least one geometrical descriptor ($\vec{e}_T$, c), and comparing said current and reference 2D characteristics by the determined geometrical descriptor.

8. The device of claim 7, wherein the geometrical descriptor further comprises a unit tangent vector ($\vec{e}_T$) to the 2D characteristic, considered at a plurality of points.

9. The device of claim 8, wherein the discriminator means further comprises means for evaluating an average angle between unit tangent vectors to respectively the current 2D characteristic and the reference 2D characteristic.

10. The device of claim 7, wherein said geometrical descriptor further comprises a norm of the velocity vector of the 2D characteristic, considered in a plurality of points.

11. The device of claim 10, wherein the discriminator means further comprises means for evaluating a correlation coefficient between the norms of the velocity vectors of respectively the current 2D characteristic and the reference 2D characteristic.

12. The device of claim 7, wherein said geometrical descriptor further comprises the curvature (c) of the 2D characteristic, considered in a plurality of points.

13. The device of claim 12, wherein the discriminator means further comprises means for evaluating a correlation coefficient between the curvature (c) of the 2D characteristic and the reference 2D characteristic.

14. The device of claim 1, wherein the bi-dimensional analysis means further comprises means for determining a reference mark orthonormal to an axis corresponding to a main axis of the patient's heart.

15. The device of claim 14, wherein means for determining said reference mark further comprises means for analyzing a sinus EGM signal wherein the EGM signal is collected in the absence of tachycardia episodes.

16. The device of claim 14, further comprising means for applying to said first and second 2D characteristics a reference change, from a primitive reference to said reference mark.

17. The device of claim 16, wherein said diagnosis means further comprises means for analyzing said main axis components and producing a first descriptor parameters of a morphology of said first and second 2D characteristics.

18. The device of claim 17, wherein said first descriptor parameters are parameters selected from the group consisting of: first and second eigen values of a covariance matrix associated to each of these eigen values; orientation of the main axis of the patient's heart and a secondary axis; a ratio between an extreme signal amplitudes on at least two channels; and an area circumscribed by the 2D characteristic.

19. The device of claim 14, wherein said diagnosis means further comprises means for producing a first and a second one-dimensional component by projection of each of said first and second 2D characteristic on one of the axis of said reference mark.

20. The device of claim 19, wherein said diagnosis means further comprises means for producing second descriptor parameters of the morphology of said first and second one-dimensional component.

21. The device of claim 20, wherein said second descriptor parameters are parameters selected from the group consisting of: a signal maximum height; a signal minimum height; and a signal width.

22. The device of claim 14, wherein said diagnosis means further comprises means for providing an inter-correlation between said first and second 2D characteristics.

23. The device of claim 1, wherein the bi-dimensional analysis means further comprises:
means for determining a reference mark orthonormal to an axis corresponding to a main axis of the patient's heart;
means for applying to said first and second 2D characteristics a reference change, from a primitive reference to said reference mark;
means for analyzing said main axis components and producing a first descriptor parameters of a morphology of said first and second 2D characteristics,
wherein said first descriptor parameters are first and second eigen values of a covariance matrix associated to each of these eigen values; and
means for providing an inter-correlation between said first and second 2D characteristics, wherein said inter-correlation means further comprises means for providing a bi-dimensional distribution analysis between the correlation coefficients and the eigen values of the covariance matrix of an analysis in principal components.

24. The device of claim 23, wherein said inter-correlation means further comprises means for providing a three-dimensional distribution analysis, able to define, for at least one descriptor parameter of the morphology of said first and second 2D characteristics, a discriminator plane between ventricular originated tachycardias and supra-ventricular originated tachycardias.

25. The device of claim 24, wherein said inter-correlation means further comprises a linear classifier means for performing said three-dimensional distribution analysis.

26. The device of claim 24, wherein said three-dimensional distribution analysis means further comprises an adaptive neural network classifier.

27. The device of claim 14, wherein diagnosis means are essentially devoid of an analysis in principle components.

28. The device of claim 27, wherein said diagnosis means further comprises means for determining ratios between a maximum amplitude and a minimum amplitude of a depolarization complex for each of said two distinct temporal components, respectively for said Sinus Rhythm and tachycardia beats.

29. The device of claim 27, wherein said diagnosis means further comprises means for determining a correlation maximum between said 2D characteristics from said Sinus Rhythm and Tachycardia beats.

* * * * *